US010017724B2

(12) United States Patent
Nikkhah et al.

(10) Patent No.: US 10,017,724 B2
(45) Date of Patent: Jul. 10, 2018

(54) ENGINEERING OF A NOVEL BREAST TUMOR MICROENVIRONMENT ON A MICROFLUIDIC CHIP

(71) Applicants: Mehdi Nikkhah, Scottsdale, AZ (US); Roger D. Kamm, Cambridge, MA (US); Danh Truong, Tempe, AZ (US)

(72) Inventors: Mehdi Nikkhah, Scottsdale, AZ (US); Roger D. Kamm, Cambridge, MA (US); Danh Truong, Tempe, AZ (US)

(73) Assignees: Arizona Board of Regents on Behalf of Arizona State University, Scottsdale, AZ (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/872,920

(22) Filed: Oct. 1, 2015

(65) Prior Publication Data
US 2016/0097027 A1    Apr. 7, 2016

Related U.S. Application Data (60) Provisional application No. 62/058,186, filed on Oct. 1, 2014.

(51) Int. Cl.
*B01L 3/00*    (2006.01)
*G01N 33/50*    (2006.01)
(Continued)

(52) U.S. Cl.
CPC ............ *C12M 23/16* (2013.01); *C12M 25/14* (2013.01); *B01L 3/502707* (2013.01);
(Continued)

(58) Field of Classification Search
CPC .............................. C12M 23/16; C12M 25/14
See application file for complete search history.

(56) References Cited

U.S. PATENT DOCUMENTS

| 2008/0102478 | A1* | 5/2008 | Li | B01L 3/5027 |
|---|---|---|---|---|
| | | | | 435/7.23 |
| 2011/0159522 | A1* | 6/2011 | Kamm | C12Q 1/02 |
| | | | | 435/7.21 |

(Continued)

OTHER PUBLICATIONS

Vickerman, et al., "Design, fabrication and implementation of a novel multi-parameter control microfluidic platform for three-dimensional cell culture and real-time imaging", Lab Chip, 2008, 8(9):1468-1477.

(Continued)

*Primary Examiner* — Jennifer Wecker
(74) *Attorney, Agent, or Firm* — Quarles & Brady LLP (57) ABSTRACT

A microfluidic device for more accurately modeling the in vitro environment in which cancer occurs is disclosed. The device comprises a surface defining one or more microfluidic channels that may further comprise one or more endothelial cells, a first three dimensional scaffold comprising one or more cancer cells that is spatially separated from the one or more microfluidic channels, and a second three dimensional scaffold comprising one or more stromal cells, at least a portion of which is interposed between the one or more microfluidic channels and the first three dimensional scaffold. The second three dimensional scaffold is in fluid communication with both the first three dimensional scaffold and the one or more microfluidic channels. The device can be used to assay anti-cancer agents, or as a system for modeling the growth, behavior, or metastasis and tumor formation of cancer cells.

20 Claims, 11 Drawing Sheets
(7 of 11 Drawing Sheet(s) Filed in Color)

(51) Int. Cl.
*C12M 3/00* (2006.01)
*C12M 1/00* (2006.01)
*C12M 1/12* (2006.01)
*C12M 3/06* (2006.01)

(52) U.S. Cl.
CPC . *B01L 3/502715* (2013.01); *B01L 2300/0816* (2013.01); *B01L 2300/12* (2013.01); *G01N 33/5011* (2013.01)

(56) References Cited

U.S. PATENT DOCUMENTS

| 2011/0186165 | A1* | 8/2011 | Borenstein | C12M 23/16 137/833 |
| 2014/0057311 | A1* | 2/2014 | Kamm | B01L 3/502753 435/29 |
| 2014/0273223 | A1* | 9/2014 | Cho | C12M 23/16 435/396 |
| 2015/0087006 | A1* | 3/2015 | Pak | C12M 23/16 435/29 |

OTHER PUBLICATIONS

Chung, et al., "Cell migration into scaffolds under co-culture conditions in a microfluidic platform", Lab Chip, 2009, 9:269-275.

Sudo, et al., "Transport-mediated angiogenesis in 3D epithelial coculture", The FASEB Journal, 2009, 23(7):2155-2164.

Farahat, et al., "Ensemble Analysis of Angiogenic Growth in Three-Dimensional Microfluidic Cell Cultures", PLoS ONE, 2012, 7(5):e37333, pp. 1-14.

Zervantonakis, et al., "Three-dimensional microfluidic model for tumor cell intravasation and endothelial barrier function", PNAS, 2012, 109(34):13515-13520.

Kalchman, et al., "A three-dimensional microfluidic tumor cell migration assay to screen the effect of anti-migratory drugs and interstitial flow", Microfluid Nanofluid, 2013, 14:969-981.

Jeon, et al., "In Vitro Model of Tumor Cell Extravasation", PLoS ONE, 2013, 8(2):e56910, pp. 1-9.

Chen, et al., "Mechanisms of tumor cell extravasation in an in vitro microvascular network platform", Integr. Biol., 2013, 5:1262-1271.

Bersini, et al., "A microfluidic 3D in vitro model for specificity of breast cancer metastasis to bone", Biomaterials, 2014, 35:2454-2461.

Shin, et al., "Extracellular Matrix Heterogeneity Regulates Three-Dimensional Morphologies of Breast Adenocarcinoma Cell Invasion", Adv. Healthcare Mater., 2013, 2:790-794.

Polacheck, et al., "Interstitial flow influences direction of tumor cell migration through competing mechanisms", PNAS, 2011, 108(27):11115-11120.

* cited by examiner

ENGINEERING OF A NOVEL BREAST TUMOR MICROENVIRONMENT ON A MICROFLUIDIC CHIP

CROSS-REFERENCE TO RELATED APPLICATIONS

This application claims the benefit of U.S. provisional Application No. 62/058,186 filed on Oct. 1, 2014, which is incorporated by reference herein in its entirety.

STATEMENT REGARDING FEDERALLY SPONSORED RESEARCH OR DEVELOPMENT

This invention was made with Government support under Grant No. R33 CA174550 awarded by the National Institutes of Health. The Government has certain rights in the invention.

BACKGROUND

Metastasis, a process where cancer cells migrate to distant organs from the primary tumor site, is the key biological process responsible for 90% of all cancer related deaths. Metastatic dissemination of cancer cells is a multi-step biological process initiated by tumor angiogenesis and invasion of the cancer cells through their surrounding stroma toward the blood vessels.

Tumor stroma is a structurally complex microenvironment hosting several cell types including endothelial cells (ECs), fibroblasts (FBs) and macrophages, packed in extracellular matrix (ECM), along with a dense network of capillaries. In this respect, the reciprocal interactions of the cancer cells with the surrounding microenvironment significantly influence their malignancy. Therefore, investigation of metastatic behavior of cancer cells in response to various microenvironmental stimuli is the key factor to identify efficient therapeutic strategies.

In the past few years, significant efforts have been devoted toward studying the mechanism of cancer metastasis, using in vivo and in vitro models. Genetically modified animal models have been crucially important to define the molecular basis of disease progression. However, using these models, there are certain difficulties to independently study the effects of various microenvironmental cues (i.e., cell-cell communication, mechanical properties of the matrix) on cancer cells metastasis. Furthermore, extensive testing of therapeutic compounds using in vivo models is a costly process.

Alternatively, in vitro assays have been widely used to study cancer cells behaviors (i.e. migration) within well-controlled experimental conditions. In vitro cell migration studies have been typically performed using 2D rigid substrates, Boyden chambers and transwell-based assays. Although these assays have facilitated high throughput and economically efficient experimental analysis, they do not fully recapitulate the complexities of the native 3D tumor microenvironment.

On the other hand, 3D macroscale ECM hydrogels and scaffolds (i.e. collagen) have shown a great promise for conducting fundamental research in cancer biology. Interestingly, such studies have demonstrated similar drug resistance profiles to those demonstrated by in vivo models. The limiting aspects of 3D macroscale hydrogel models are the lack of precise control over cellular distribution, lack of vascularity and difficulties in establishing stable chemical gradients throughout the 3D matrix for potential drug screening applications.

Recent advances in micro- and nanoscale (i.e. micropatterning, microfluidics) technologies have enabled the development of innovative platforms to study cancer cell migration within well defined 3D microenvironments. Despite significant progress, most of the previously developed platforms have relied on simplified models to study the effects of a limited number of microenvironmental cues (i.e., matrix elasticity) on cancer metastasis. For instance, only a few studies have incorporated stromal cells (i.e. macrophages, FBs) within their model to recapitulate a physiologically relevant tumor microenvironment.

The breast tumor microenvironment is a complex milieu consisting of numerous cells types including fibroblasts and immune cells, packed in extracellular matrix (ECM), along with a dense network of capillaries. While previous research has demonstrated that the crosstalk between the cancer cells and their surrounding microenvironment significantly influences their metastatic potential, the success of therapeutic approaches to suppress breast tumor progression has been insufficient. A critical challenge in efficient translation of therapeutic strategies to clinical practice is the lack of physiologically relevant tumor models to study metastatic dispersion of cancer cells in response to microenvironmental stimuli within well-controlled experimental conditions.

Accordingly, due to the complexities associated with the native tumor stroma, there is an unmet need to develop physiologically relevant model in vitro microenvironments, in order to explore the metastatic behavior of cancer cells in response to a wide range of biophysical and biochemical stimuli.

BRIEF SUMMARY

To address these challenges, we developed an innovative approach using microscale technologies and hydrogel based biomaterials to develop a three dimensional (3D) in vivo like breast tumor microenvironment on a microfluidic chip. Specifically, we used microengineering technology, hydrogel-based biomaterials, and co-culture of key cell types within the tumor stroma to develop an in vivo like 3D vascularized human breast tumor model microenvironment. Hydrogels are excellent scaffolding materials because of their 3D architecture resembling the native in vivo microenvironment, homogenous cellular distribution, excellent diffusion properties and tunable mechanical characteristics. To date, hydrogels have been extensively used to study vascularization/angiogenesis, cell invasion and tissue morphogenesis. Integration of microscale (i.e. microfluidics) technology and biology not only offers high throughput systems but also enables tight control of the cellular microenvironment by varying cell-cell, cell-substrate, and cell-soluble factors interactions. Using microfabrication techniques, it is possible to create precisely defined features and organized cellular constructs to address the limitations of the conventional 2D assays and 3D macroscale hydrogel constructs.

Surrounding stroma embedded with inflammatory and immune cell (i.e. FBs, macrophages) plays a crucial role in cancer progression. In particular, FBs have been shown to exhibit activated phenotype with significantly higher proliferation and ECM deposition (collagen I) within the tumor stroma. Moreover, there have been studies demonstrating the FBs and inflammatory cells are principal source of host-derived VEGF secretion, which result in increased vascular permeability and ultimately enhanced angiogenesis within the tumor microenvironment. Therefore, co-culture of FBs, macrophages and ECs along with metastatic breast cancer cells provides a promising path to assess the influence of other cells types on cancer migration through the surrounding stroma. The unique features of the disclosed devices and methods bridge the gap between conventional 2D/3D assays and animal models to recapitulate the complexities associated within the native tumor stroma.

Accordingly, in a first aspect, the disclosure encompasses a microfluidic device that includes (a) a surface defining one or more microfluidic channels; (b) a first three dimensional scaffold comprising one or more cancer cells that is spatially separated from the one or more microfluidic channels; and (c) a second three dimensional scaffold, at least a portion of which is interposed between the one or more microfluidic channels and the first three dimensional scaffold. The second three dimensional scaffold is in fluid communication with both the first three dimensional scaffold and the one or more microfluidic channels.

In some embodiments, the cancer cells are breast cancer cells. In some embodiments, the one or more cancer cells are metastatic or tumorigenic cancer cells. In some such embodiments, the one or more metastatic or tumorigenic cancer cells are metastatic or tumorigenic breast cancer cells.

In some embodiments, the second three dimensional scaffold comprises one or more stromal cells. In some such embodiments, the one or more stromal cells are fibroblasts. In some embodiments, the second three dimensional scaffold comprises one or more macrophages.

In some embodiments, one or more of the microfluidic channels include one or more endothelial cells. In some such embodiments the endothelial cells form a monolayer in the on the surface of the microfluidic channel.

In some embodiments, the first three dimensional scaffold, the second three dimensional scaffold, or both comprise a gel matrix. In some such embodiments, the gel matrix comprises one or more of the group consisting of collagen, fibronectin, hyaluronan, a hydrogel, a peptide gel, and a gel-like protein, or interpenetrating network hydrogels. In some such embodiments, the gel matrix comprises a collagen hydrogel.

In some embodiments, the surface comprises a polymer. In some such embodiments, the polymer is polydimethylsiloxane (PDMS) or poly(methylmethacrylate) (PMMA).

In some embodiments, the surface extends beyond the one or more microfluidic channels, and the extended surface underlies both the first and second three dimensional scaffolds.

In some embodiments, at least a portion of the surface is patterned. In some embodiments, the surface further includes microposts separating the one or more microfluidic channels from the second three dimensional scaffold.

In some embodiments, the device further includes one of more inlets for adding the first three dimensional scaffold, the second three dimensional scaffold, or both to the microfluidic device.

In some embodiments, the microfluidic channels include one or more fluidic inlets suitable for introducing a test agent into the microfluidic device.

In some embodiments two microfluidic channels are disposed along two opposite sides of the second three dimensional matrix.

In some embodiments, the one or more cancer cells are obtained directly from a cancer patient in need of treatment.

In a second aspect, the disclosure encompasses a method of assaying a test agent for anti-cancer activity. The method includes the steps of (a) providing a microfluidic device as described above; (2) introducing the test agent to the microfluidic device through the one or more fluidic inlets; and (3) observing the cancer cells within the microfluidic device to determine the effect of the test agent.

In some embodiments, the cancer cells are obtained directly from a patient in need of treatment.

In a third aspect, the disclosure encompasses a method of studying cancer or related cells. The method includes the steps of (1) providing a microfluidic device as described above; and (2) observing one or more of the cancer cells, stromal cells, or epithelial cells within the microfluidic device.

In some embodiments, the method further includes the steps of altering one or more microenvironments within the microfluidic device, and determining the effect of the alteration on the one or more cells.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, non-limiting exemplary methods and materials are described herein.

A major challenge in treatment of metastatic disease is the lack of suitable tumor models to test the efficacy of various therapeutic compounds in a high throughput and combinatorial fashion. Unfortunately, there are notable limitations associated with the previously reported tumor models. Genetically modified animal models (i.e. mouse) have been crucially important to define the molecular basis of disease progression; however, there are certain difficulties in distinguishing the effects of various micro environmental cues on disease progression. Furthermore, in many scenarios, the main components of these models are mouse origin, while only the tumor cells are of human origin.

On the other hand, a large body of previously reported in vitro assays have used two dimensional (2D) platforms under mono-culture conditions. Other limitation of in vitro models include the use of immortalized or commercially available cell lines rather than patient derived primary cells. The development of preclinical in vivo like tumor models using clinical samples is particularly appealing in personalized medicine, as there is a significant heterogeneity within the population of cancer cells derived from patients.

To address these challenges, we disclose herein using microengineering technology, hydrogels, and patient specific primary cells to develop a three dimensional (3D) breast tumor microenvironment on a chip. Our platform facilitates clinically translatable techniques to study cancer cell line as well as patient specific tumor metastasis. In addition, the proposed platform can be independently used to assess the effects of various therapeutic compounds on cancer cells metastasis in a combinatorial and high throughput manner. We envision that the proposed technology will have an enormous impact on the lives of numerous patients suffering from breast cancer, through the development of personalized therapeutic regimens.

Accordingly, we disclose herein using hydrogel-based biomaterials and microfabrication/microfluidics technologies to precisely engineer a 3D biomimetic human breast tumor microenvironment on chip to study the malignant behavior of cancer cells within three specific stages including: a) Dissemination from the primary tumor region, b) Migration through the surrounding matrix and c) Intravasation.

There are four major innovative aspects disclosed herein. First, the disclosed approach utilizes an integrative strategy to merge microscale technology and hydrogels to develop a 3D tumor model. While, there has been extensive amount of effort toward the development of in vitro assays to study the malignancy of breast cancer cells, most of the previously reported platforms have been limited in terms of simplified culture conditions, such as using two dimensional (2D) surfaces or static growth environment. A major challenge in using such assays is the interpretation of the outcome, as these assays significantly deviate from the native microenvironment cancer cells experience. Herein, we disclose using hydrogels, as excellent scaffolding materials, to provide a 3D microenvironment to support cellular function. Furthermore, through the use of microengineering technology, we can precisely control the location of tumor construct and the surrounding stroma. For example, using the disclosed devices, we can localize cancer cells within a well defined 3D hydrogel constructs and precisely engineer a neoplastic lesion, which is primarily isolated from the surrounding microenvironment. The microfluidic platform will provide a perfusable system where it would be possible to accurately control the culture condition and the distribution of the soluble factors throughout the hydrogel construct in a real time fashion.

Second, the proposed platform has enormous potential to be incorporated with patient specific primary cells and fresh tumor biopsies rather than just relying on the use of immortalized and commercially available cell lines. Our strategy is particularly appealing, since the use of patient derived primary cell provides a strategy toward more personalized, more effective and less toxic treatment to breast cancer patients. In particular, we can selectively use a single microengineered chip to study the drug responsiveness of cancer patients in combinatorial therapeutic regimens. Furthermore, the proposed technology provides a solid foundation to overcome the challenges associated in cancer therapy due to heterogeneous population of tumor cells derived from individual patients.

Third, the majority of the previously reported in vitro assays have been founded on the use of single cell types (i.e. metastatic cancer cells). However it is becoming well recognized that the surrounding stroma embedded with fibroblasts and inflammatory/immune cell plays a crucial role in cancer progression. Particularly, numerous studies have demonstrated that the cross-talk through paracrine signaling between cancer cells and the stromal cells, such as fibroblasts, significantly influence their malignancy. As a result, there is an increasing interest toward exploring novel therapeutic compounds targeting the tumor microenvironment.

Unfortunately previous studies have not incorporated the crucial components of the native tumor microenvironment in their model system.

In the disclosed systems, we have modeled these complexities while developing a physiologically relevant tumor microenvironment to study metastatic cells dissemination and migration of the cancer cells.

In some of the exemplary embodiments disclosed herein, fibroblast cells and macrophages are incorporated within the model tumor microenvironment. However, a central feature of our approach is the modularity of the proposed platforms in terms of: a) flexibility in the selection of appropriate biomaterials with variable stiffness and porosity to construct the 3D tumor microenvironment, and b) inclusion of other cell types such as immune/inflammatory cells, endothelial cells. Overall, with the disclosed design, we will be able to tune the complexity of the proposed platform toward the targeted study.

Fourth, the disclosed microengineered platform allows recovering samples from different locations of the chip, in order to assess the correlation between the genetic heterogeneity of cancer cells to their migration profile within the 3D hydrogel constructs.

This disclosure is directed to a microfluidic device that includes one or more microfluidic channels and two different three dimensional scaffolds, each three dimensional scaffold containing, e.g., a 3D gel matrix contained within a chamber of the microfluidic device. The first three dimensional scaffold includes encapsulated cancer cells, while the second three dimensional scaffold may include encapsulated stromal cells, such as fibroblast cells, and may further include macrophages. At least a portion of the second three dimensional scaffold is interposed between the first three dimensional scaffold and the one or more one or more microfluidic channels. The interposed second three dimensional scaffold is in fluid communication with (i.e., fluidically coupled with) both the microfluidic channels and the first three dimensional scaffold.

A microfluidic channel, as the terms is used herein, typically has a channel width perpendicular to a longitudinal axis of the channel (i.e., a path along which fluid flows during ordinary operation) that is about 1 mm or smaller. In general, the channel width depends on the particular application. For example, for creating cellular monolayers, channel widths may range, in certain non-limiting embodiments, from about 200 µm to about 1200 µm, from about 300 µm to about 1100 µm, from about 400 µm to about 1000 µm, or from about 400 µm to about 600 µm. The cross-sections of the microchannels (perpendicular to the respective longitudinal axes) may be rectangular, round, or have any other shape, and may (but need not) vary in size or shape along the longitudinal axes.

The three dimensional scaffolds allow fluid flow and cell migration through the scaffolds, between the scaffolds, and between the scaffolds and the microfluidic channels (i.e., the three components are in "fluid communication" with each other). Thus, in embodiments having two different microfluidic channels on opposite sides of the microfluidic device, by establishing fluid flows in the two microfluidic channels that differ in their respective pressures and/or the concentrations of one or more fluid constituents (e.g., a pharmaceutical compound, biochemical factor, etc.), a pressure and/or concentration gradient may be established across the 3D scaffolds. In certain embodiments, the two microfluidic channels may have separate or common inlets, but merge downstream the 3D scaffold to share a common outlet. As a result, the pressures in the two channels are substantially equalized, such that a pressure gradient across the 3D scaffold is avoided, as is desired for some applications. At the same time, a controlled concentration gradient can be established across the 3D scaffolds by injecting fluids of different compositions at the inlets upstream of the scaffolds.

In some embodiments, the microfluidic device may have non-uniformly treated and/or patterned interior surfaces. The interior surface of a microfluidic device includes the walls of the microfluidic channels, as well as the walls of any other hollow spaces formed in the polymer (or other solid) structure defining the device, such as, e.g., the walls of the gel-holding chamber. Surface treatment and/or patterning include chemical and/or topographical surface modifications. Chemical modifications, in turn, include treatments and/or coatings with inorganic substances as well as with organic substances (such as, e.g., antibodies or proteins). Non-uniform surface treatment implies that one or more portions of, but less than the entire, surface is treated, or that different portions are treated in different ways.

Patterning implies repetitive (although not necessarily perfectly regular) surface modifications. For example, in some embodiments, one or more microchannel walls may feature chemically (including, e.g., biologically) treated islands, or non-treated islands defined by an otherwise treated surface area. Further, in some embodiments, certain interior surfaces are topographically structured, e.g., with microposts. Microposts disposed at the top and bottom surfaces of a gel-containing chamber may serve to hold the gel in place. Further, microposts and other topographical structures may be used to influence the interactions of cells with the walls. Microposts at oblique angles to the surface may, for instance, be used to adjust the apparent "softness" of the walls for purposes of cell-wall interactions.

The microfluidic devices as described herein may be used for culturing and observing cells in a controlled microenvironment. Applications include, for example, cell migration, proliferation, and differentiation studies (e.g., angiogenesis investigation), and the analysis of biophysical and biochemical factor influence on cell function (including, e.g., drug safety and efficacy testing). Commercial applications of the devices described herein include, but are not limited to, evaluating cancer therapies, quantifying cancer cell migration, testing pharmaceuticals, and individualizing an anti-cancer treatment to a specific patient's tumor type.

The three dimensional scaffolds may include or consist essentially of a gel matrix, which may comprise a gel or gel-like material such as, e.g., collagen, fibronectin, hyaluronan, a hydrogel (such as, e.g., polyethylene glycol hydrogel), a peptide gel, or gel-like proteins or protein mixtures secreted by animal cells (e.g., Matrigel™) as well as interpenetrating network hydrogels. Non-limiting examples of polymers that can be used to construct the disclosed microfluidic devices include polystyrene, polydimethylsiloxane, polycarbonate, poly(methyl methacrylate), cyclic olefin copolymer, polyethylene, polyethylene terephthalate, polyurethane, polycaprolactone, polylactic acid, polyglycolic acid, or poly(lactic-co-glycolic acid). In some embodiments, different types of polymers are used for different components or portions of the polymer structure. The polymer structure may be substantially optically transparent (e.g., have a transmission in the visible range of more than 70%, preferably more than 90%, and more preferably more than 95%).

In certain embodiments, the upper and/or lower surface of the chamber that contains the three dimensional scaffolds may features surface modifications, which may serve to hold the scaffolds in place. For example, the surface(s) may be modified with microposts disposed thereon. Further, in some embodiments, the surface(s) of one or both microchannels, or one or more surface portions, are patterned (e.g., chemically or topographically). The surface patterning may be non-uniform.

The invention will be more fully understood upon consideration of the following non-limiting Example.

EXAMPLES

Example 1

An Exemplary Microfluidic Device

In this example, we describe a non-limiting exemplary embodiment of a microfluidic device according to the disclosed invention.

Figure 1:
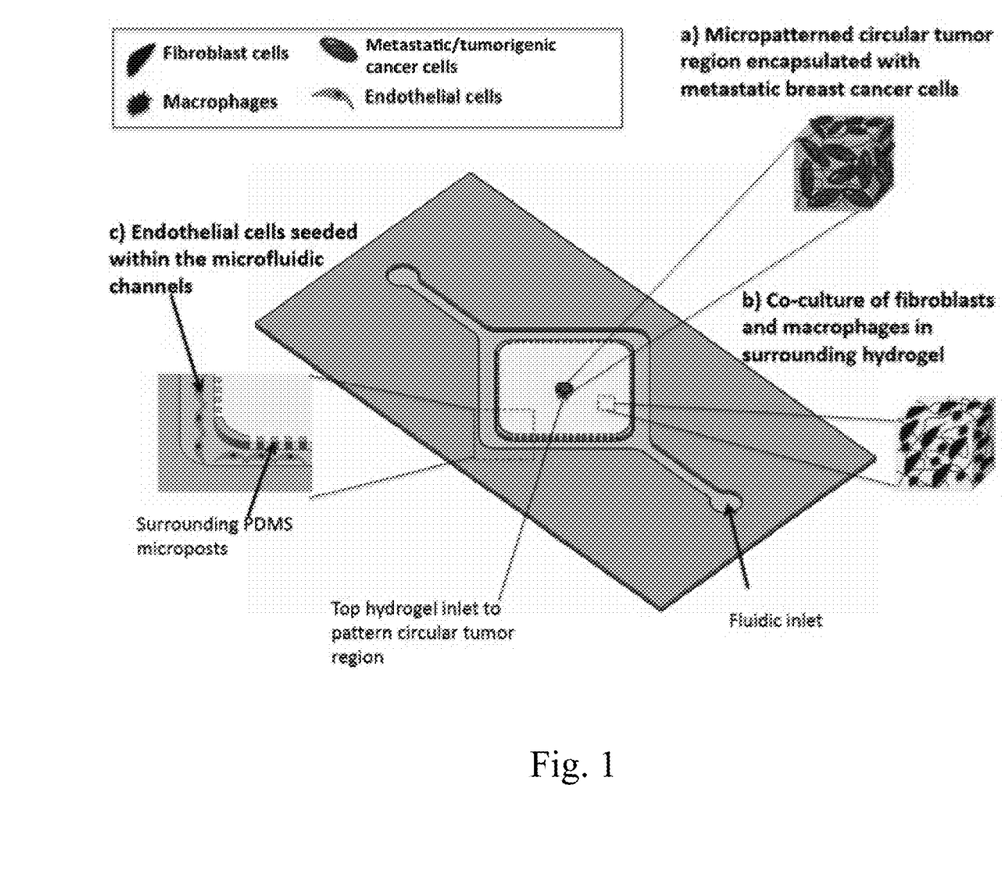
FIG. 1 is a schematic top view of a first exemplary microfluidic device.

FIG. 1 shows the features of the exemplary microfluidic device, As shown in FIG. 1, the microfluidic device includes two separate regions of hydrogel constructs, one for the circular tumor construct (neoplastic lesion) encapsulated with metastatic breast cancer cells ((a); center circle), and the second one resembling the surrounding 3D ECM stroma for encapsulation of FBs and macrophages ((b); rectangle surrounding center circle). Two parallel microfluidic channels seeded with ECs are interconnected with the surrounding ECM hydrogel ((c), adjacent to the two long edges of rectangle of (b)). In particular, the microfluidic channels will be used for seeding of ECs resembling the vascular network ((c)). In addition, the microfluidic channels will be used to introduce anticancer drugs for testing.

Microfluidic Device.

The preliminary design of the exemplary microfluidic device can be performed using AutoCAD, based on the following dimensions:

| Design designation | Channel length/width/height | Surrounding hydrogel dimensions | Micropost Spacing |
| --- | --- | --- | --- |
| A | 8 mm/500 µm/150 µm | 4 mm × 4 mm | 100 µm |
| B | 6 mm/500 µm/150 µm | 3 mm × 3 mm | 100 µm |
| C | 5 mm/500 µm/150 µm | 2.5 mm × 2.5 mm | 100 µm |
| D | 6 mm/500 µm/150 µm | 3 mm × 3 mm | 150 µm |

The exemplary microfluidic devices may be fabricated in polydimethylsiloxane (PDMS) using replica molding technique. For drug testing applications, other hydrophilic materials, such as functionalized Poly(methylmethacrylate) (PMMA), may be used instead of PDMS to fabricate the device. However, the fabrication process would be similar to that used for PDMS.

Briefly, transparency masks, design by AutoCAD (minimum features of 20 µm), are used for SU-8 photolithography to create the silicon wafer master. PDMS and the curing agent are mixed in 10:1 (base:curing) ratio, and the solution is poured over the silicon wafer master, degassed and put in an 80° C. oven for 2 h. Upon polymerization, PDMS wafer is peeled off from the silicon wafer master, and each microfluidic device is cut.

The inlet and outlets may be cored down to the microfluidic channels using a standard 1 mm diameter punch. Prior to cell culture experiments, the microfluidic device is sterilized in 120° C. for 20 min in a wet cycle, followed by a dry cycle at 120° C. for 35 min. The PDMS surfaces of the microfluidic device is rendered hydrophilic by using air plasma to enhance hydrogel loading within the device, according to previously published procedures.

Finally, the PDMS devices are each bonded to a glass cover slip through oxygen plasma treatment. The edges of the hydrogel injection channels may be tapered in order to reduce bubble formation.

Cell Encapsulation and Hydrogel Injection.

Collagen type I (or alternative) hydrogel may be used for cellular encapsulation and construction of the 3D microenvironment. The lyophilized protein is dissolved in 0.02 N acetic acid to obtain a collagen solution with 1-4 mg/ml concentration. Breast carcinoma (i.e. MDA-MB-231) expressing mCherry fluorescent protein, human umbilical vein endothelial cells (HUVECs) expressing green fluorescence protein, human mammary FBs and human macrophage cell line U937 may be used in this work.

FBs and macrophages may be encapsulated in a collagen hydrogel (surrounding stroma, FIG. 1), with the densities of $3.2 \times 10^6$ and $0.8 \times 10^6$ cells/ml (ratio 4:1), respectively. The surrounding hydrogel can be injected from the inlets located at the top. Upon gel injection, the device is placed inside the humidified incubator for 30 min at 37° C., in a 5% $CO_2$ atmosphere, to polymerize the hydrogel construct.

Cancer cells may be encapsulated in collagen hydrogel prepolymer solution with the density of $0.5 \times 10^6$ cells/ml of hydrogel. A punch is used to core the center of the device creating a circular indentation in the stroma. The cell encapsulated hydrogel can be slowly injected from the top inlet of the microfluidic device, using image guided phase contrast microscopy and a microfluidic pump. (see FIG. 1).

Upon gel injection, the device is placed inside the humidified incubator for 30 min at 37° C., in a 5% $CO_2$ atmosphere, to polymerize the hydrogel construct. After hydrogel cross-linking, ECs may be seeded though the side channels with the density of $2 \times 10^6$/ml of media. As the stiffness of the soft breast tissue to stiff tumor is within the range of 0.2-4 kPa, the concentration of the collagen hydrogel may be varied (e.g., from 1-4 mg/ml), in order to tune the mechanical properties of the surrounding stroma.

Evaluation of the Platform Performance.

The formation of EC monolayer through the microfluidic channels may be assessed through staining the GFP-expressing ECs with CD-31 and VE-cadherin cellular junction protein after 48 h of culture. Primary and secondary Alexa Fluor conjugated 595 secondary antibodies specific to human ECs (Abcam) may be used to for staining of CD-31 and VE-cadherin. Cell-cell junctions may be carefully visualized through high magnification (40×) fluorescence microscopy, and the fluorescence intensity of cellular junctions may be measured using NIH Image J software. These analyses will ensure successful seeding and coverage of the ECs within the inner layer of the microfluidic channels, thus resembling the vascularized networks.

To test the perfusion capacity of the microfluidic device and establishment of stable gradients of soluble factors through the surrounding hydrogel construct, Texas Red-conjugated Dextran (70 kDa, Invitrogen), diluted in EC basal media (concentration: 12.5 µg/mL) may be flowed through the channels at the rate of 1 mL/min. The gradient and the diffusion profile of the fluorescence molecules through the surrounding collagen hydrogel may be detected using real time fluorescence microscopy. The obtained fluorescent intensity data enables measurement of diffusive EC permeability (PD) according to the previously developed computational model: $PD = \beta \cdot D/\Delta C(dC/dx)$, where C is the dextran concentration (proportional to fluorescence intensity), $\Delta C$ the step drop in concentration across the monolayer (obtained from raw fluorescence data), β is an area correction factor, dC/dx is the slope of the concentration profile, and D is the dextran diffusion coefficient ($9 \times 10^{-11}$ m²/s).

The permeability 48 h post seeding of ECs within the microfluidic channels may be measured for two time points (e.g., within 24 h and 48) within ten separate regions of the surrounding hydrogel in between the microfluidic channels and the circular tumor construct. Characterization of permeability may be validated through computational finite element modeling using COMSOL software.

Example 2

Production and Use of an Exemplary Microfluidic Device

In this proof of principal example, we demonstrate that a microfluidic device according to the disclosed invention is capable producing a well-defined tissue architecture, and that it enables high-contrast and real-time imaging for detailed invasion and intravasion studies.

Introduction.

The development of our breast cancer invasion platform has given our laboratory the opportunity to investigate and provide insight to key aspects of the metastatic cascade and tumorigenesis. This study validates our model as breast cancer invasion and demonstrates that our platform is capable of producing a well-defined tissue architecture and enabling high-contrast real-time imaging for detailed invasion and intravasation studies.

Creating a Spatially Organized Cancer Invasion Platform.

Figure 2A:
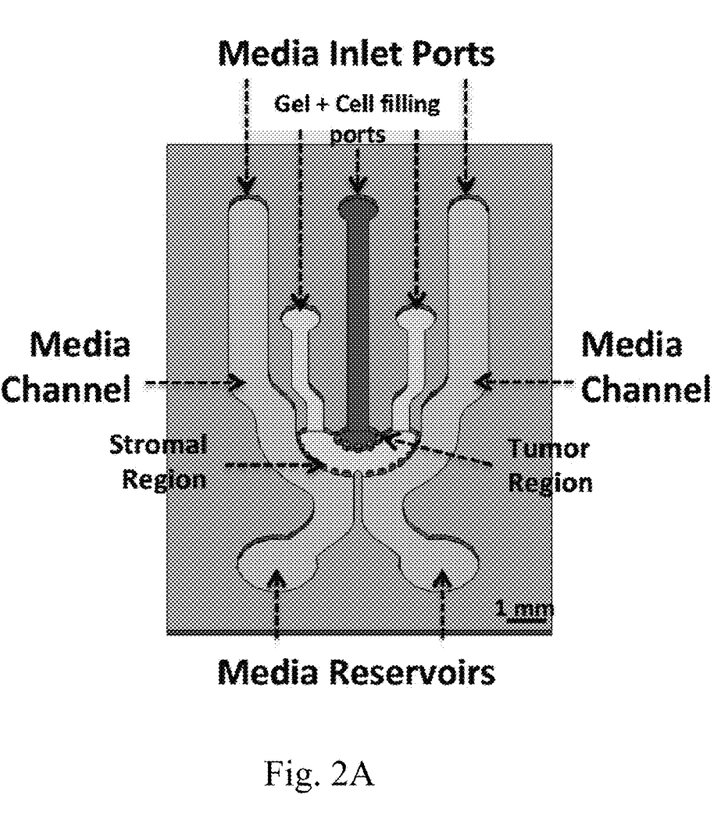
FIG. 2A is a schematic top view of a second exemplary microfluidic device.
Figure 2B:
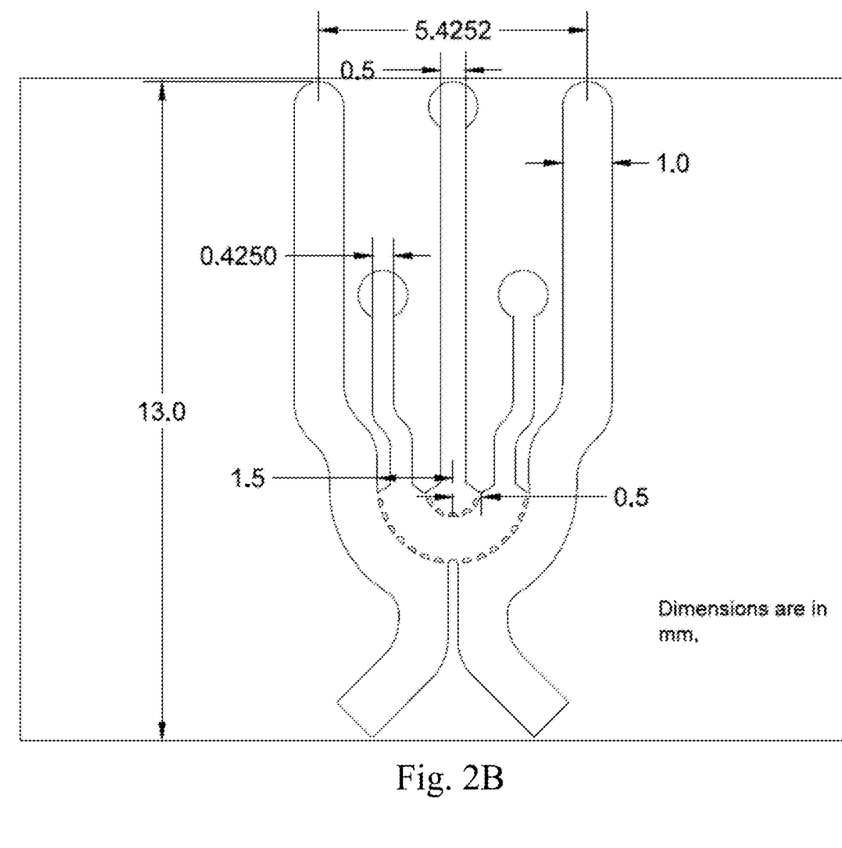
FIG. 2B is a schematic top view of one embodiments of the second exemplary microfluidic device, showing selected dimensions in millimeters (mm).
Figure 2C:
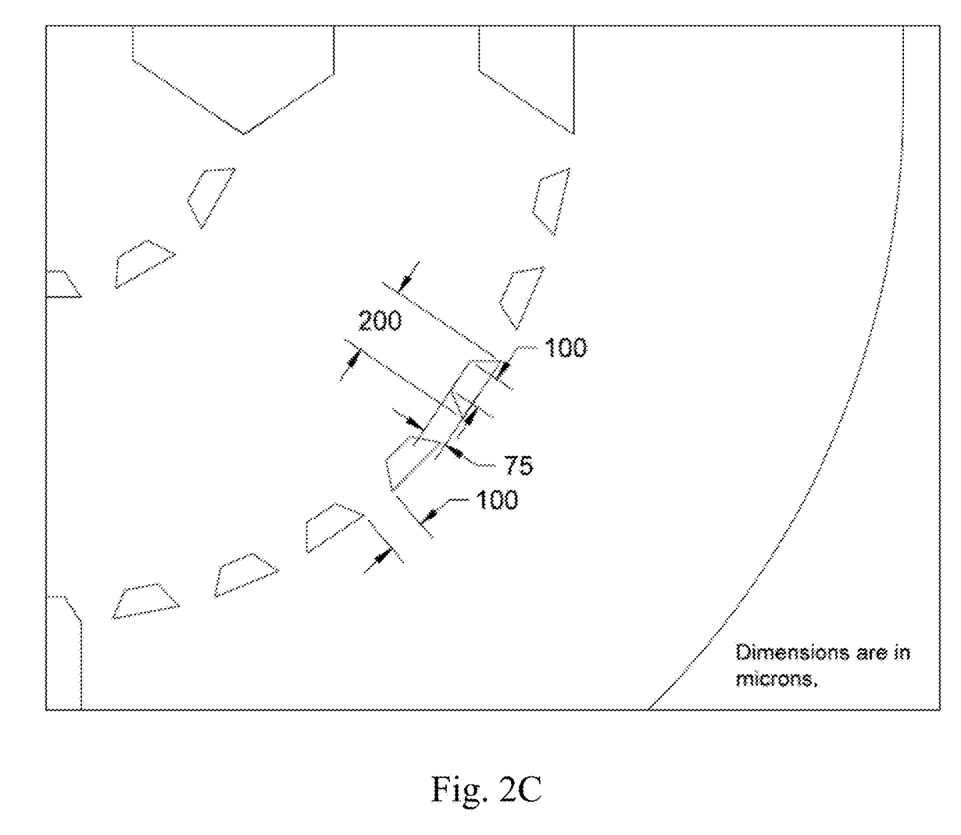
FIG. 2C is a schematic top view showing an enlarged section of FIG. 2B that includes the right half of the tumor and stromal regions and an associated section of the right media channel. Selected dimensions are shown in microns (μm).

First, we developed a CAD design that caters to the native breast tumor architecture (FIG. 2A). It consisted of two distinct region made up of two concentric semi-circles. The inner semi-circle represents the tumor region whereas the outer semi-circle represents the stromal region. We set the radius for the inner circle to be 0.5 mm and the radius for the outer circle was 1.5 mm. Additionally, there are two channels that flank the stromal region representing vascularized networks. The channels had a width of 1 mm and the final depth of the chambers was 200 microns. We used microposts comprising of trapezoids to confine the hydrogel matrix within the tumor and stromal regions based on the surface contact angle of collagen gel to PDMS (see FIGS. 2B and 2C).

Demonstrating Defined Regions within the Platform.

Figure 3:
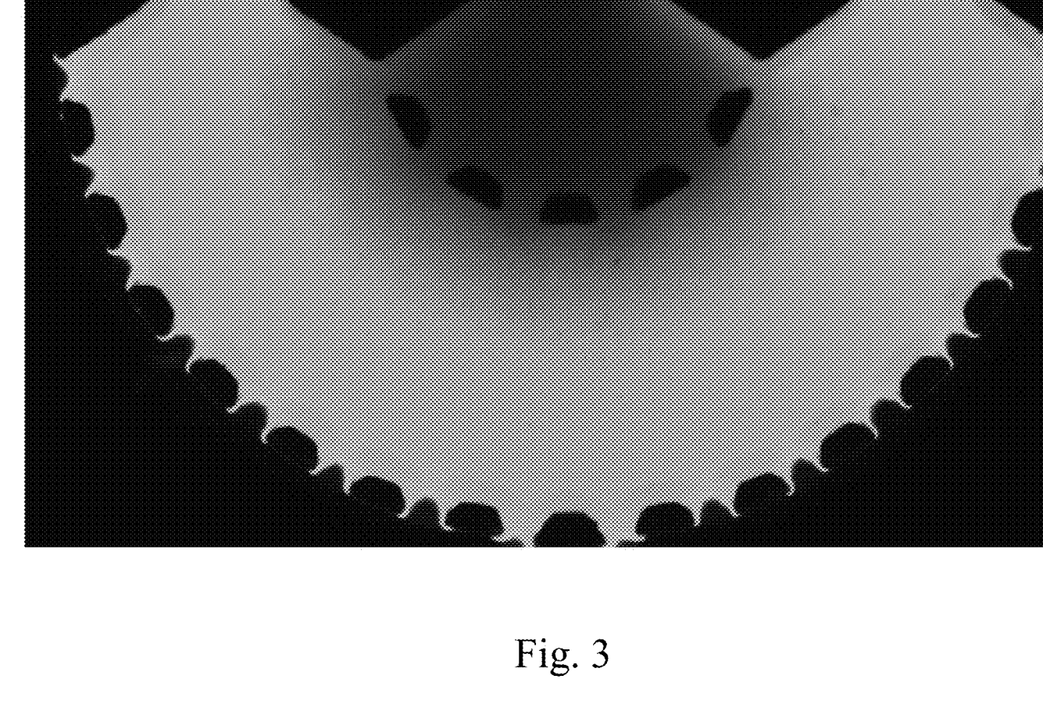
FIG. 3 is a photographic top view of a section of the second exemplary microfluidic device. A dark red dyed hydrogel defines the tumor regions and a green dyed hydrogel defines the stromal region.
Figure 4:
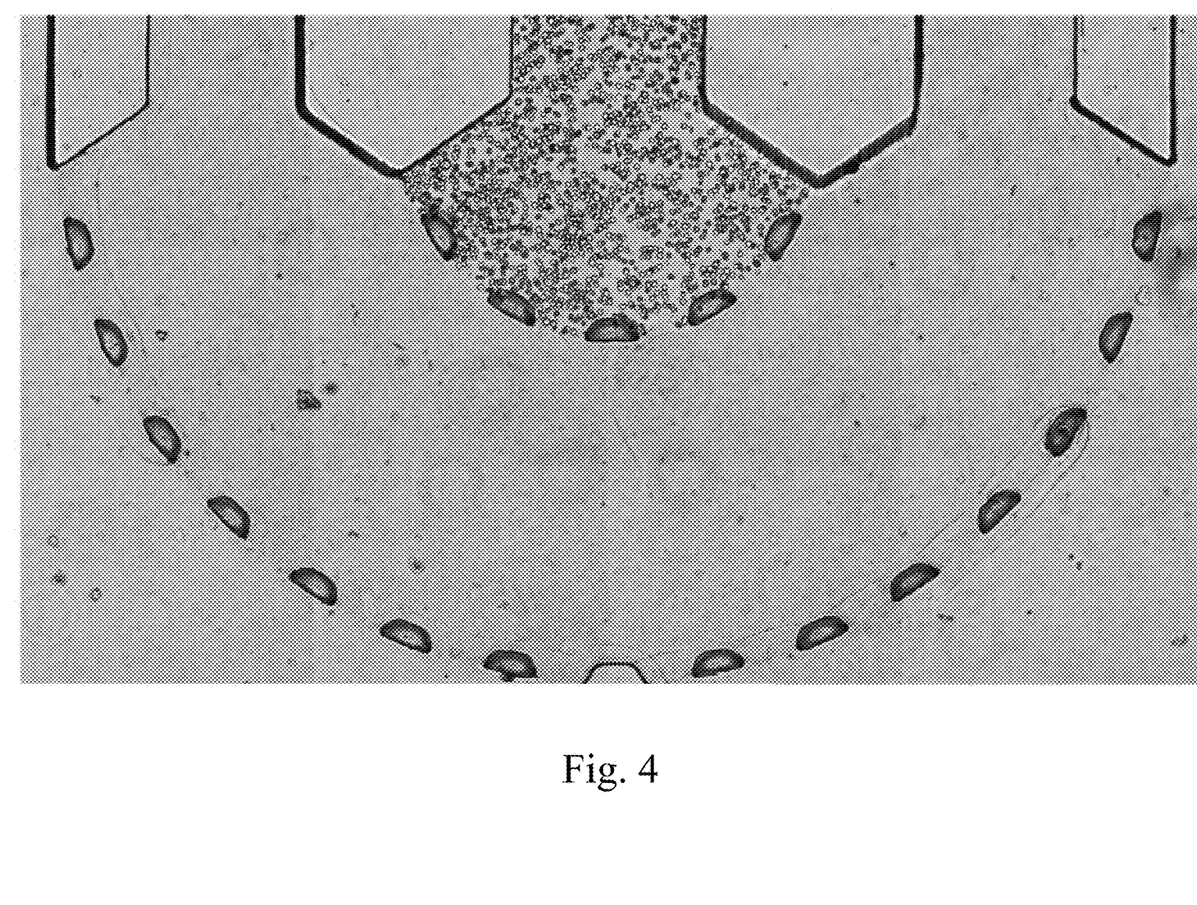
FIG. 4 is a photographic top view of a section of the second exemplary microfluidic device. Cancer cells are confined within the tumor region and cell-free collagen is confined within the stromal region.

We used a dyed hydrogel and injected it into the device to demonstrate the feasibility of creating defined regions within our platform (FIG. 3). By doing so, this implies that there can be two different hydrogels consisting of different cells, ECM proteins, stiffness, and growth factors arranged spatially. Furthermore, we validated this fact by injecting the tumor region with SUM-159 breast carcinoma cells encapsulated in collagen and subsequently injecting the stromal region with cell-free collagen (FIG. 4). In this regard, we demonstrated a clearly defined interface between the two regions of different composition representing the typical breast tumor architecture.

Characterizing Biomolecular Gradients.

Figure 5:
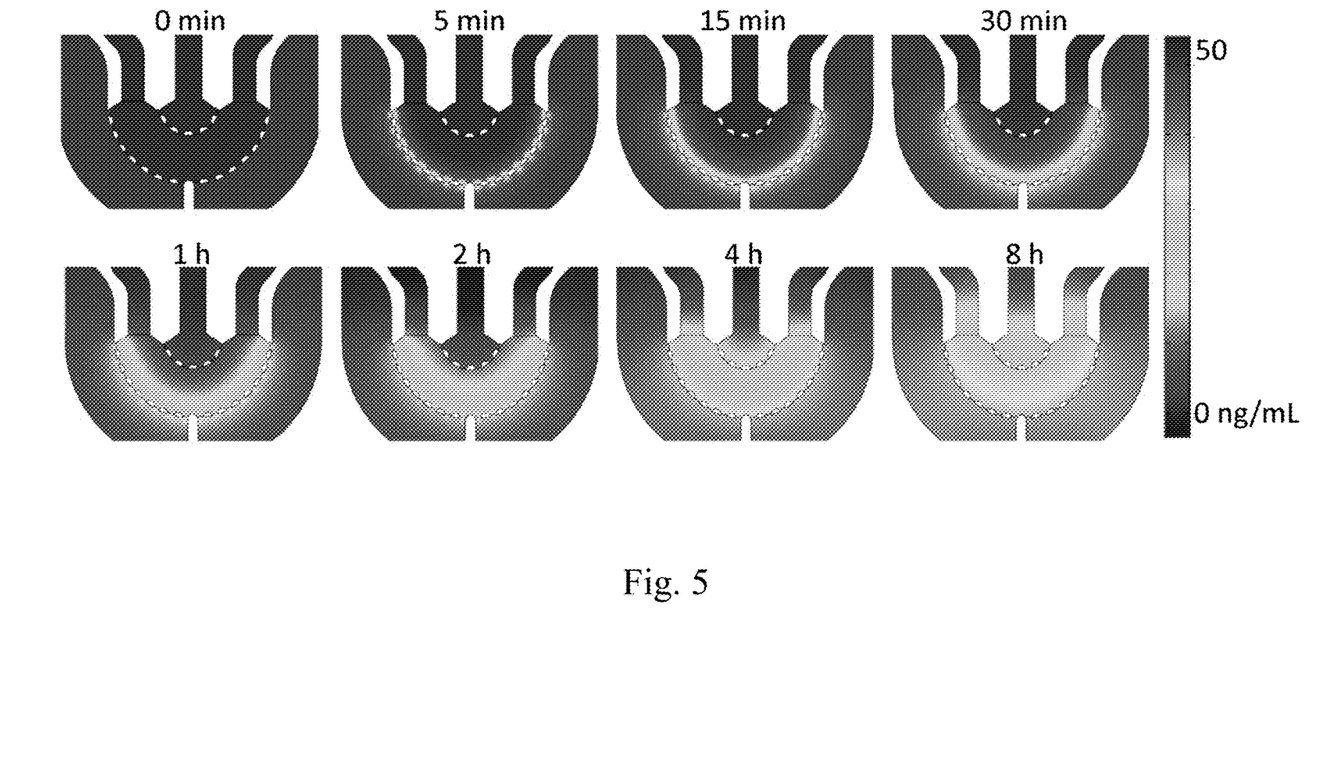
FIG. 5 is a software-generated model showing the development of a diffusive gradient over time in the second exemplary microfluidic device.

To show a steady chemogradient in our platform, we performed computational modeling to assess diffusion gradients using COMSOL Multiphysics software. The Stokes-Einstein equation was used to calculate diffusion coefficients for molecules of various molecular weights. For our device, we used 2 mg/mL of collagen type I as the encapsulating matrix. For the simulation, we used a 10 kDa molecule as a reference point and 50 ng/mL of the molecule was simulated diffusing into the tumor region. A stable gradient was established in the tumor region by 4 h (FIG. 5).

Chemoinvasion of Breast Cancer Cells.

We encapsulated highly invasive SUM-159 breast cancer cells within our platform. Cells were encapsulated in a mixture of Collagen:Matrigel at a ratio of 1:1 (final collagen density is 1 mg/mL) and the solution was injected into the tumor region while cell-free collagen type I (2 mg/mL) was injected into the stromal region. In one platform, 50 ng/mL of epidermal growth factor (EGF) was injected to the side channels to stimulate chemoinvasion, while in a control platform, no EGF was injected. We observed the migration of the cells throughout the stromal region over the course of four days in both conditions.

Figure 6:
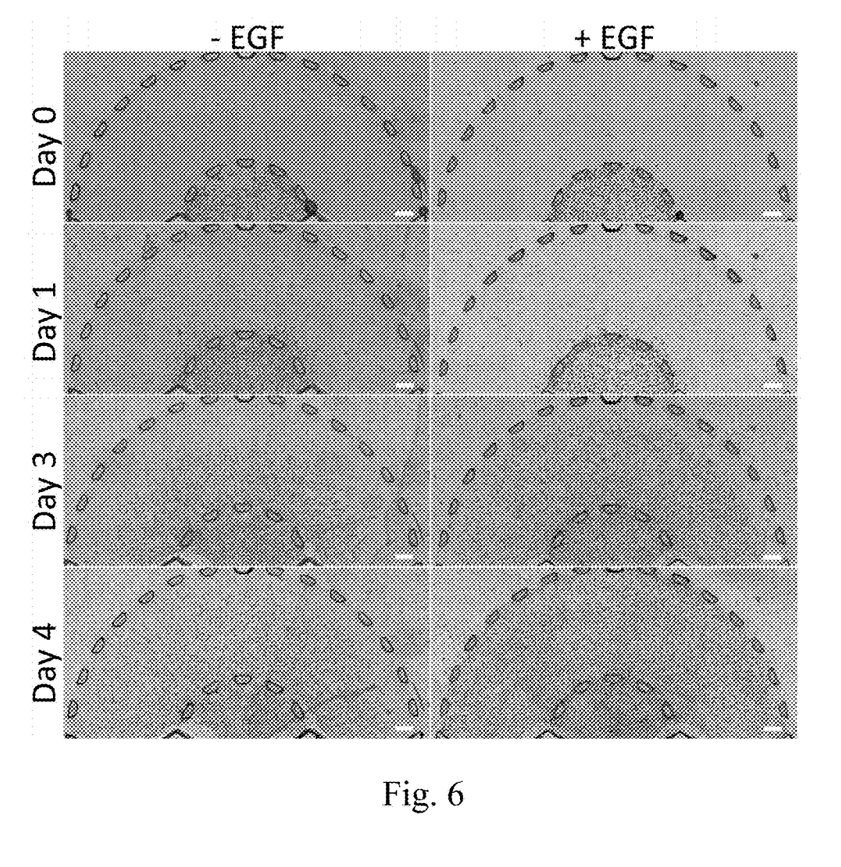
FIG. 6 is a series of photographs showing invasion of SUM-159 breast cancer cells over time within a section of the second exemplary microfluidic device. Chemoinvasion stimulated by epithelial growth factor (+EGF, right column) is compared to invasion of unstimulated control cells (−EGF, left column).
Figure 7:
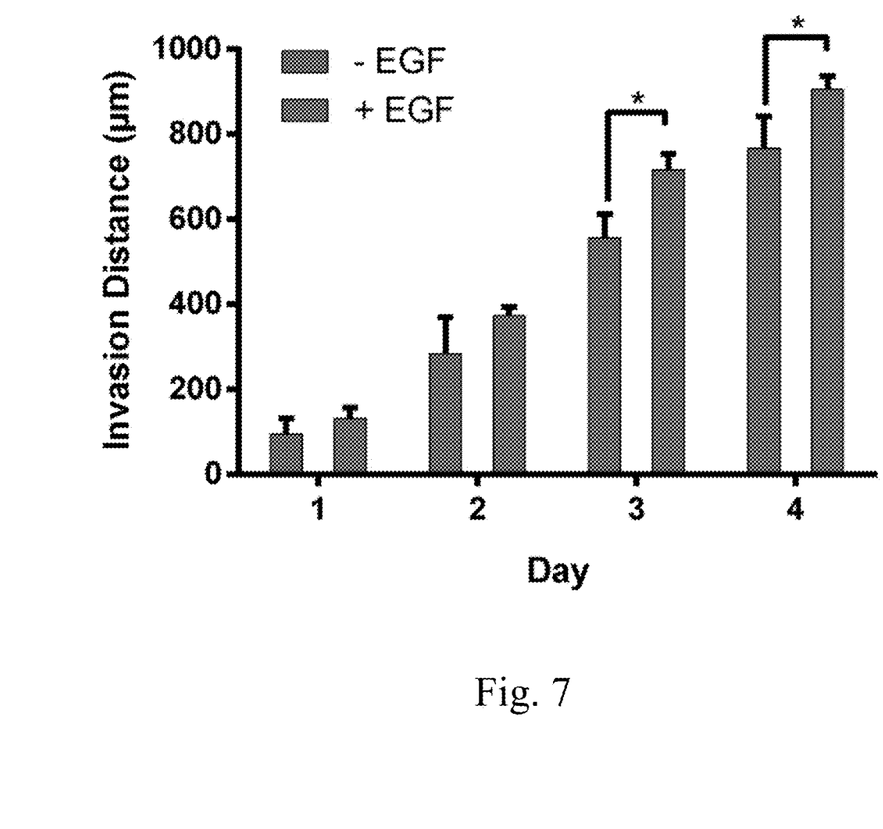
FIG. 7 is a graph showing invasion distance in μm as a function of days after SUM-159 breast cancer cell introduction within the second exemplary microfluidic device. Results are shown for both chemostimulated (red, +EGF) and unstimulated (blue, −EGF) trials.
Figure 8:
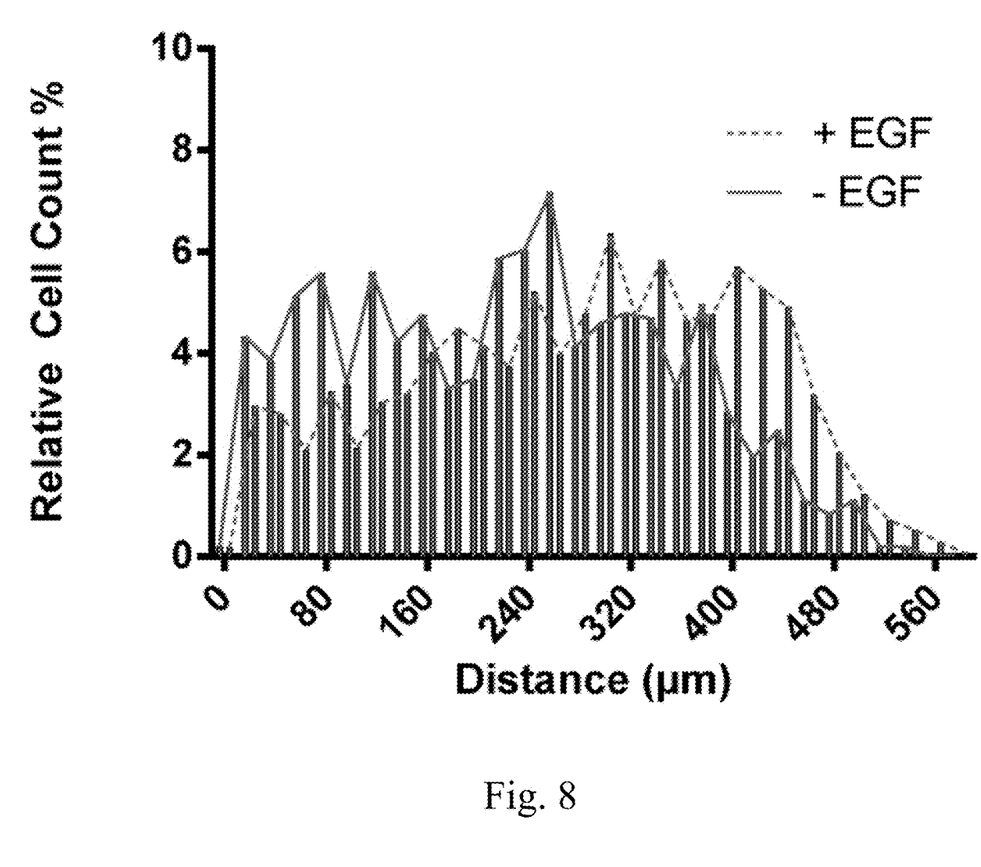
FIG. 8 is a graph showing relative cell count (as percent of total cells) as a function of migration distance four days after SUM-159 breast cancer cell introduction within the second exemplary microfluidic device. Results are shown for both chemostimulated (red, +EGF) and unstimulated (blue, −EGF) trials.
Figure 9:
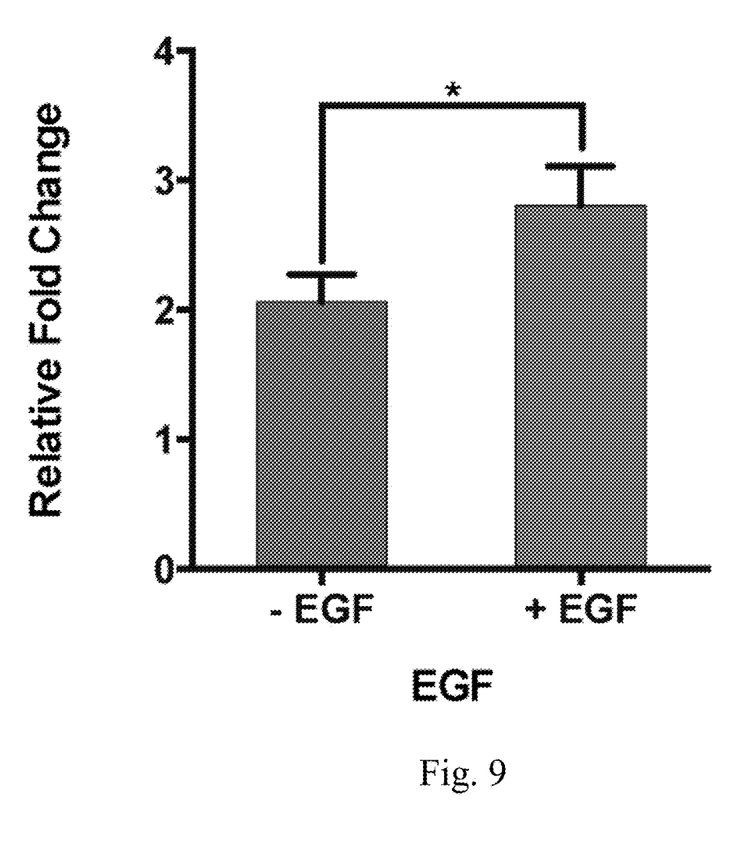
FIG. 9 is a graph showing fold change in SUM-159 breast cancer cell within the media channels of the second exemplary microfluidic device between three and four days after cell introduction within the second exemplary microfluidic device. Results are shown for both chemostimulated (red +EGF) and unstimulated (blue −EGF) trials.

As seen in FIG. 6, cells under both conditions began to invade the stromal region after one day. There was noticeable collagen deformation showing that the cells are actively sensing their biophysical environment and reacting to it. Additionally, cells within the tumor region demonstrated a round morphology while cells that invaded the stromal region demonstrated spindle-like morphology. By day 3, it was evident that cells stimulated by EGF invaded further (FIG. 7). Cells without EGF stimulation did invade as well but not by the same distance. By day 4 in the EGF stimulated group, more cells had migrated a greater distance (FIG. 8), and a higher number of cells were seen in the channels as compared to the −EGF control group (FIG. 9).

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A microfluidic device, comprising:
   a surface defining one or more microfluidic channels, wherein the surface extends beyond the one or more microfluidic channels;
   a first three dimensional scaffold comprising one or more cancer cells that is not in direct contact with the one or more microfluidic channels;
   a second three dimensional scaffold, at least a portion of which is directly contacting the one or more microfluidic channels and the first three dimensional scaffold, and which is in direct fluid communication with both the first three dimensional scaffold and the one or more microfluidic channels,
   wherein the first three dimensional scaffold, the second three dimensional scaffold, or both comprise a gel matrix; and
   wherein the extended surface underlies both the first and second three dimensional scaffolds.

2. The microfluidic device of claim 1, wherein the one or more cancer cells are metastatic or tumorigenic cancer cells.

3. The microfluidic device of claim 1, wherein the one or more cancer cells are breast cancer cells.

4. The microfluidic device of any of claim 1, wherein the second three dimensional scaffold comprises one or more stromal cells.

5. The microfluidic device of claim 4, wherein the one or more stromal cells are fibroblasts.

6. The microfluidic device of claim 1, wherein the second three dimensional scaffold comprises one or more macrophages.

7. The microfluidic device of claim 1, wherein one or more of the microfluidic channels comprises one or more endothelial cells.

8. The microfluidic device of claim 1, wherein the gel matrix comprises one or more of the group consisting of collagen, fibronectin, hyaluronan, a hydrogel, a peptide gel, a gel-like protein or interpenetrating network hydrogels.

9. The microfluidic device of claim 1, wherein the gel matrix comprises a collagen hydrogel.

10. The microfluidic device of claim 1, wherein the surface further comprises microposts separating the one or more microfluidic channels from the second three dimensional scaffold.

11. The microfluidic device of claim 1, further comprising one of more inlets for adding the first three dimensional scaffold, the second three dimensional scaffold, or both to the microfluidic device.

12. The microfluidic device of claim 1, wherein one or more of the microfluidic channels comprises one or more fluidic inlets suitable for introducing a test agent into the microfluidic device.

13. The microfluidic device of claim 12, comprising two microfluidic channels disposed along two opposite sides of the second three dimensional matrix.

14. The microfluidic device of claim 1, wherein the one or more cancer cells are obtained directly from a cancer patient in need of treatment.

15. A method of assaying a test agent for anti-cancer activity, comprising:
   introducing the test agent to the microfluidic device of claim 12 through the one or more fluidic inlets; and
   observing the cancer cells within the microfluidic device to determine the effect of the test agent.

16. The method of claim 15, wherein the cancer cells are obtained directly from a patient in need of treatment or commercially available cells lines.

17. A method of studying cancer or related cells, comprising:
   observing one or more of the cancer cells or related cells within the microfluidic device of claim 1.

18. The method of claim 17, further comprising the steps of altering one or more microenvironments within the microfluidic device and determining the effect of the alteration on the one or more cancer cells or related cells.

19. A microfluidic device, comprising:
a surface defining two microfluidic channels and extending beyond the two microfluidic channels;
a first three dimensional scaffold comprising one or more cancer cells that is not in direct contact with the two microfluidic channels;
a second three dimensional scaffold, at least a portion of which is directly contacting the two microfluidic channels and the first three dimensional scaffold, and which is in direct fluid communication with both the first three dimensional scaffold and the two microfluidic channels;
wherein the surface underlies both the first and second three dimensional scaffolds; and
wherein the two microfluidic channels are disposed along two opposite sides of the second three dimensional scaffold.

20. A microfluidic device, comprising:
a surface defining two microfluidic channels and extending beyond the two microfluidic channels;
a first three dimensional scaffold comprising one or more breast cancer cells that is not in direct contact with the two microfluidic channels;
a second three dimensional scaffold comprising stromal cells, at least a portion of which is directly contacting the two microfluidic channels and the first three dimensional scaffold, and which is in direct fluid communication with both the first three dimensional scaffold and the two microfluidic channels;
one of more inlets for adding the first three dimensional scaffold, the second three dimensional scaffold, or both to the microfluidic device;
wherein the first three dimensional scaffold and the second three dimensional comprise a gel matrix;
wherein the surface further comprises microposts separating the one or more microfluidic channels from the second three dimensional scaffold
wherein the surface underlies both the first and second three dimensional scaffolds; and
wherein the two microfluidic channels are located on along two opposite sides of the second three dimensional scaffold.

* * * * *